United States Patent
Zhuang et al.

(10) Patent No.: US 9,128,007 B2
(45) Date of Patent: *Sep. 8, 2015

(54) METHOD AND APPARATUS FOR DISTURBANCE DETECTION

(71) Applicant: OPTELLIOS, INC., Newtown, PA (US)

(72) Inventors: Zhizhong Zhuang, Bensalem, PA (US); Yuri Zadorozhny, Morrisville, PA (US); Francesco Anthony Annetta, Princeton, NJ (US); Jay S. Patel, Newtown, PA (US)

(73) Assignee: OPTELLIOS, INC., Newtown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/196,852

(22) Filed: Mar. 4, 2014

(65) Prior Publication Data

US 2014/0185037 A1 Jul. 3, 2014

Related U.S. Application Data

(63) Continuation of application No. 13/016,814, filed on Jan. 28, 2011, now Pat. No. 8,705,020.

(60) Provisional application No. 61/337,176, filed on Jan. 30, 2010.

(51) Int. Cl.
*G01N 21/00* (2006.01)
*G01M 11/00* (2006.01)
(Continued)

(52) U.S. Cl.
CPC ........... *G01M 11/33* (2013.01); *G01D 5/35361* (2013.01); *G01K 11/32* (2013.01);
(Continued)

(58) Field of Classification Search
CPC ... H04B 10/07; H04B 10/071; H04B 10/0771
USPC ....................................... 356/73.1; 398/9–16
See application file for complete search history.

(56) References Cited

U.S. PATENT DOCUMENTS 5,194,847 A 3/1993 Taylor et al.
5,567,933 A 10/1996 Robinson et al.
(Continued)

OTHER PUBLICATIONS

Mermelstein et al. "Rayleigh scattering optical frequency correlation in a single-mode optical fiber". Optics Letters; vol. 26, No. 2, 2001.*
(Continued)

*Primary Examiner* — Kara E Geisel
*Assistant Examiner* — Hina F Ayub
(74) *Attorney, Agent, or Firm* — Oblon, McClelland, Maier & Neustadt, L.L.P.

(57) ABSTRACT

A sweep sensor may include a signal source, a propagation medium, and a detector. By transmitting an interrogating signal from the signal source into the propagation medium, detectable disturbances along the medium can physically alter the characteristics of the medium, which may cause a measurable change in the backscattered signal at the detector. Based on the change, it may be possible to locate the geographic origins of the physical disturbances along the propagation medium, or to determine the nature of the disturbances, or both. For example, it is generally possible to estimate the approximate distance between the detector and the disturbance given the time required to obtain the backscattered signal and the velocity of the signal source in the propagation medium. Further, in some embodiments, it is possible to quantify the amount of disturbance.

20 Claims, 10 Drawing Sheets

(51) Int. Cl.
*G01D 5/353* (2006.01)
*G01K 11/32* (2006.01)
*G01M 5/00* (2006.01)

(52) U.S. Cl.
CPC ......... *G01M 5/0025* (2013.01); *G01M 5/0033* (2013.01); *G01M 5/0066* (2013.01); *G01M 5/0091* (2013.01); *G01N 2201/0886* (2013.01)

(56) References Cited

U.S. PATENT DOCUMENTS

| | | |
|---|---|---|
| 7,274,441 B2 | 9/2007 | Payton |
| 8,705,020 B2 * | 4/2014 | Zhuang et al. ............... 356/73.1 |
| 2004/0227930 A1 | 11/2004 | Ingles et al. |
| 2005/0002017 A1 | 1/2005 | Haran |
| 2005/0147341 A1 | 7/2005 | Patel et al. |
| 2007/0253662 A1 | 11/2007 | Patel et al. |
| 2008/0088846 A1 | 4/2008 | Hayward et al. |
| 2010/0014071 A1 | 1/2010 | Hartog |
| 2010/0302531 A1 | 12/2010 | Huffman et al. |

OTHER PUBLICATIONS

Jay S. Patel, Non-proprietary Project Abstract, Distributed fiber-optic sensing technology for civil infrastructure management, Dec. 29, 2009, 1 page.

Imahama, Mutsumi et al., Restorability of Rayleigh Backscatter Traces Measured by Coherent OTDR with Precisely Frequency-Controlled Light Source, IEICE Trans. Commun., vol. E91-B, No. 4, Apr. 2008, 4 pages.

Mermelstein, Marc D. et al., Rayleigh scattering optical frequency correlation in a single-mode optical fiber, Optics Letters, vol. 26, No. 2, Jan. 15, 2001, 3 pages.

Koyamada, Yahei et al., Fiber-Optic Distributed Strain and Temperature Sensing With Very High Measurand Resolution Over Long Range Using Coherent OTDR, Journal of Lightwave Technology, vol. 27, No. 9, May 1, 2009, 5 pages.

Optellios Inc., Fiber Patrol FP1100-X, Self-Healing Fense Intrusion Detection System, Mar. 26, 2009, 2 pages.

Optellios, Section 28 16 43 Perimeter Security Systems, FiberPatrol FP1100-X Cut Immune Location Sensing Intrusion Detection System Chain Link Fence and Mixed Applications, Architectural and Engineering Specifications, Jun. 8, 2009, 13 pages.

* cited by examiner

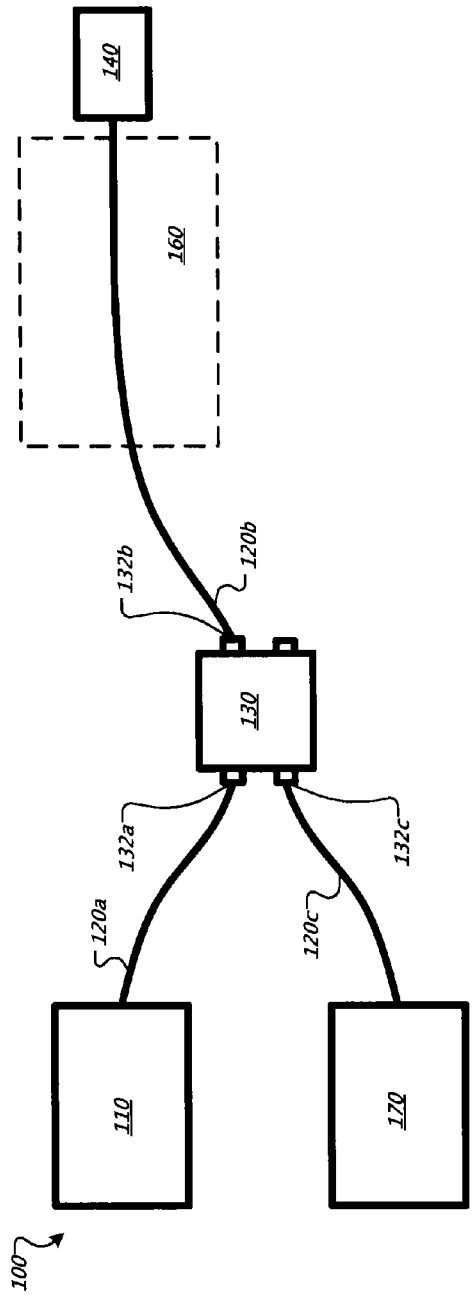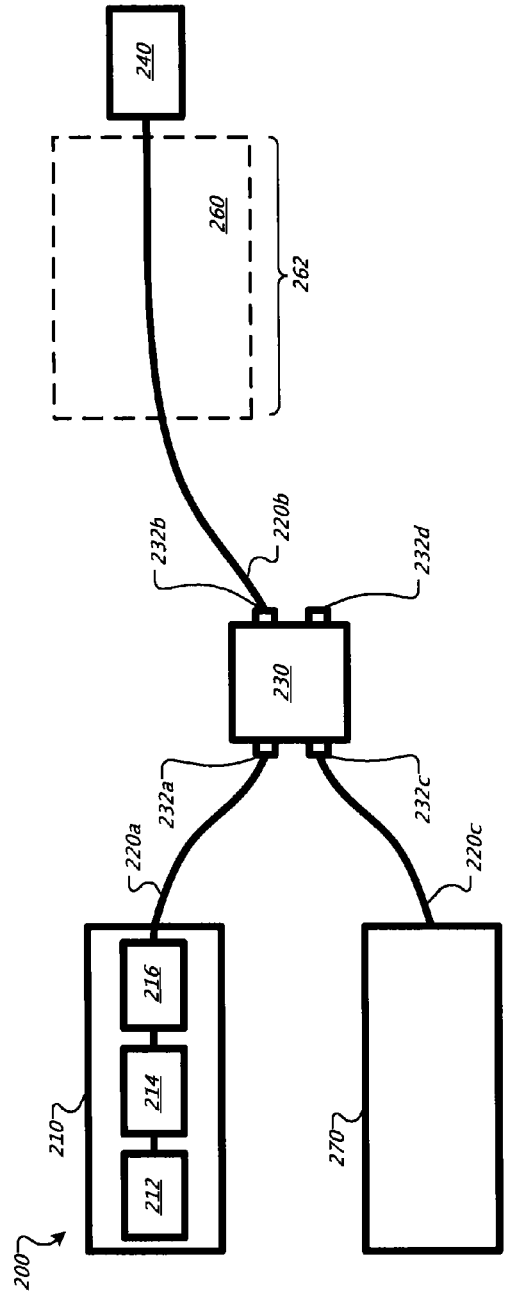
FIG. 1
FIG. 2

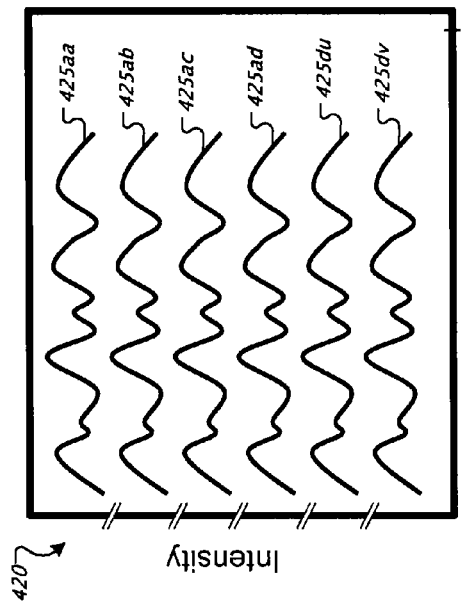
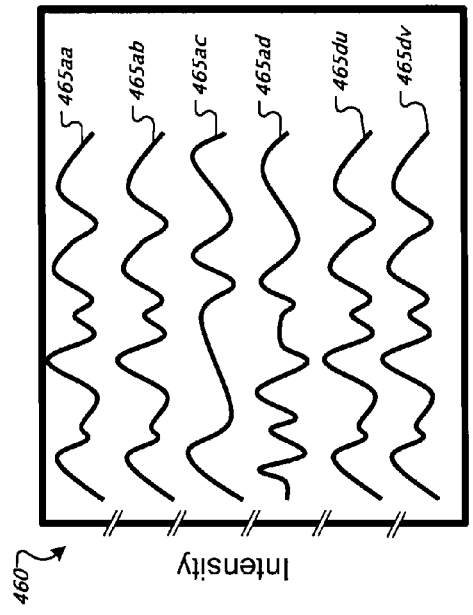
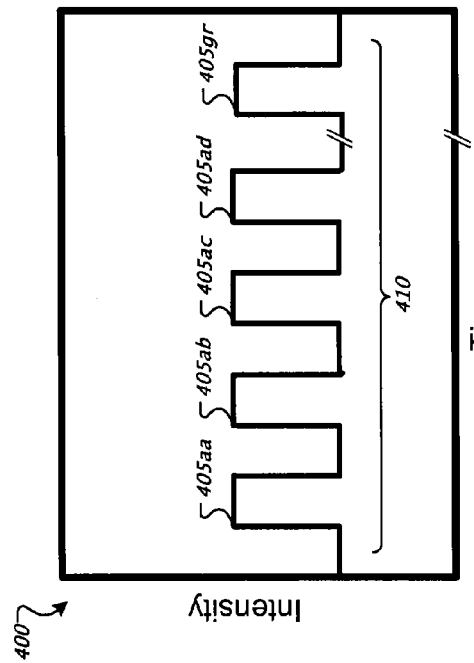
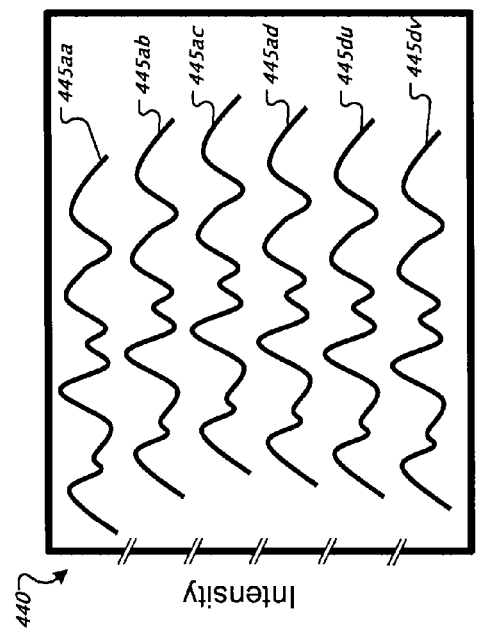
FIG. 4A
FIG. 4B
FIG. 4C
FIG. 4D

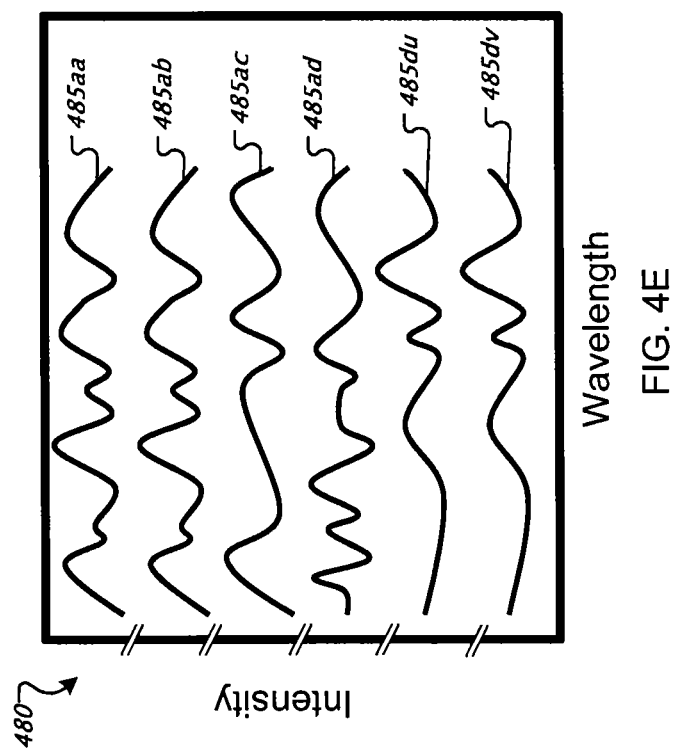

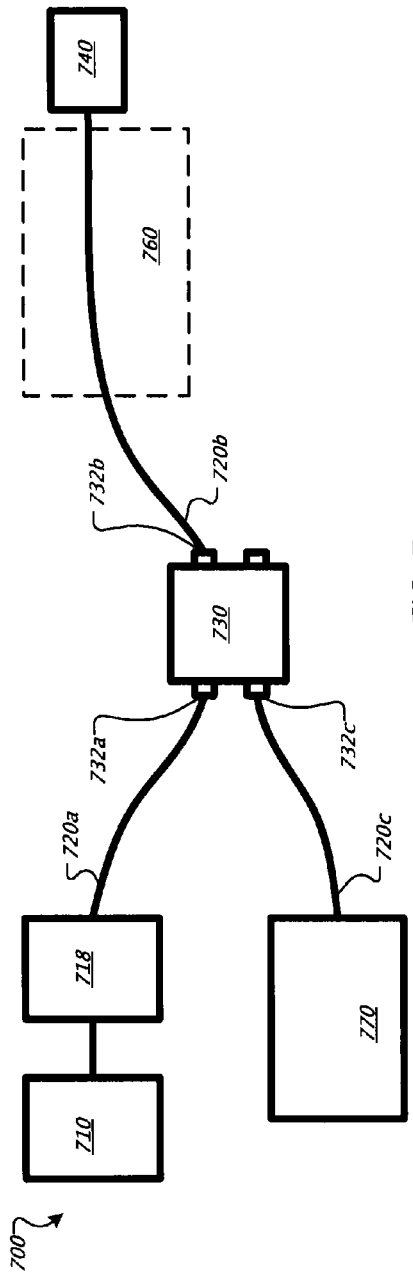
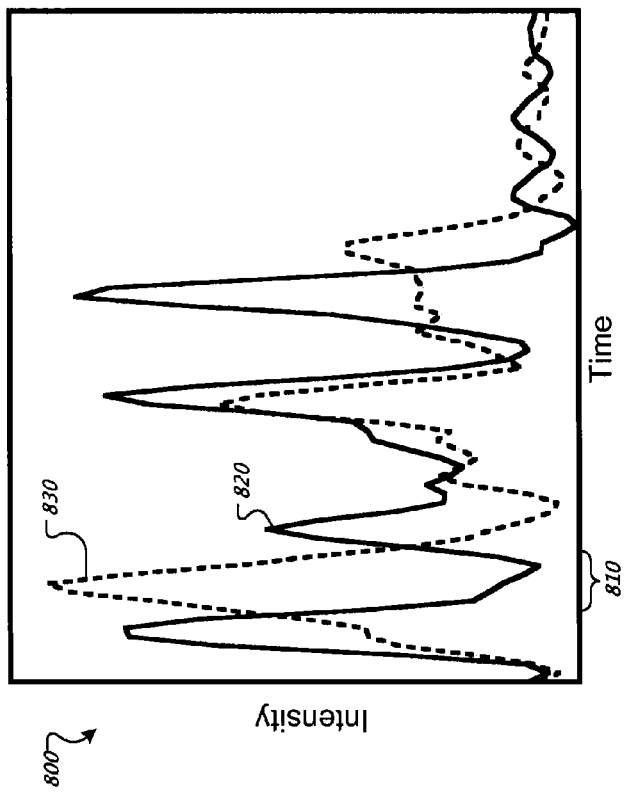
FIG. 7
FIG. 8

METHOD AND APPARATUS FOR DISTURBANCE DETECTION

CROSS-REFERENCE TO RELATED APPLICATIONS

This application is a continuation of U.S. patent application Ser. No. 13/016,814 entitled "Method and Apparatus for Disturbance Detection" filed on Jan. 28, 2011, which claims the priority benefit of U.S. Provisional Application No. 61/337,176 entitled "Fiber optic sensor" filed on Jan. 30, 2010, and is related to the commonly assigned U.S. Pat. No. 7,725,026 filed on Apr. 1, 2005 entitled "Phase responsive optical fiber sensor" and U.S. Provisional Application Nos. 61/000,968 entitled "Fiber optic intrusion detection system based on coherent OTDR" filed on Oct. 30, 2007, 61/065,600 entitled "Distributed fiber optic perimeter intrusion detection system with failover capability" filed on Feb. 13, 2008, 61/069,496 entitled "Distributed michelson intrusion detection sensor" filed on Mar. 14, 2008, 61/195,762 entitled "Distributed fiber intrusion detection sensor" filed on Oct. 10, 2008, 61/195,763 entitled "Local time series reconstruction for distributed fiber sensor" filed on Oct. 10, 2008, 61/207,274 entitled "Distributed fiber optic sensor" filed on Feb. 10, 2009, 61/283,019 entitled "Wavelength sweep fiber optic sensor" filed on Nov. 25, 2009, and 61/335,575 entitled "Wavelength sweep fiber optic sensor" filed on Jan. 8, 2010, each of which is hereby incorporated by reference in its entirety.

BACKGROUND

Fiber optics may be used as a waveguide for a coherent light wave propagating over a long distance. The refractive indices of the fiber optics may be different along the cable, and cause the light wave to travel at non-uniform speeds. Inherent built-in defects, physical perturbation, and temperature fluctuations may cause the refractive indices of a fiber optic to change. As a coherent light wave propagates through the fiber optics, the localized change of refractive indices may alter the speed of the light wave, which results in phase changes, and may cause the direction of propagation to reverse through scattering. Additionally, the birefringence of the fiber optic may cause the state of polarization of the light wave to change. In a fiber optic system, the input of the fiber optics may be aligned, both in space and the angle of approach, with output of the light source to facilitate the efficient injection of the light wave. More than one fiber optics may be fused together at their ends to increase the overall length of the waveguide.

Fiber optics can provide propagation mediums for single mode or multi-mode lasers, and are inherently immune to electromagnetic interference. For single mode transmission, the fiber optic line may have a smaller diameter than the fiber optic line for multi-mode transmission.

A fiber optic cable includes at least one fiber optic, typically made from the transparent glass fiber, in its core, and surrounded by transparent cladding with a lower index of refraction. The cable further includes a protect sleeve covering the cladding to minimize physical damages to the fiber optic line. A single cable can include one or more fiber optics. Fiber optics have the advantage of being a low-loss waveguide, and can relay optical signals over a long range without the need to amplify the signals. Some fiber optics may be doped with different materials for specialized purposes.

SUMMARY OF SELECTED EMBODIMENTS

A sweep sensor may include a signal source, a propagation medium, and a detector. By transmitting an interrogating signal from the signal source into the propagation medium, detectable disturbances along the medium can physically alter the characteristics of the medium, which may cause a measurable change in the backscattered signal at the detector. Based on the change, it may be possible to locate the geographic origins of the physical disturbances along the propagation medium, or to determine the nature of the disturbances, or both. For example, it is generally possible to estimate the approximate distance between the detector and the disturbance given the time required to obtain the backscattered signal and the velocity of the signal in the propagation medium. Further, in some embodiments, it is possible to quantify the amount of disturbance. In some implementations, the sweep sensor may be deployed as an intrusion detection sensor around the perimeter of a restricted area, for example an airport, a nuclear power plant, or a military base, to alert the security personnel of any unauthorized entry. Such implementations may place the propagation medium underground or along a fence. In other implementations, the sweep sensor may be disposed substantially close to fluid-transporting pipes, such as petroleum or natural gas pipes, to detect encroachment, excavation, leaks, and breaks. In another implementation, the sweep sensor may be deployed as a temperature sensor for applications such distributed fire detection, pipeline leak detection, or downhole sensing.

BRIEF DESCRIPTION OF DRAWINGS

FIG. 1 illustrates an implementation of a sweep sensor.
FIG. 2 shows another implementation of a sweep sensor.
FIGS. 4A-E show examples of transmitted interrogating pulses and detected traces of a sweep sensor system.
FIG. 7 illustrates an implementation of a sweep sensor which includes polarization management.
FIG. 8 shows example signals with polarization fading and with polarization management to reduce fading.

DETAILED DESCRIPTION OF ILLUSTRATIVE EMBODIMENTS

Figure 3A:
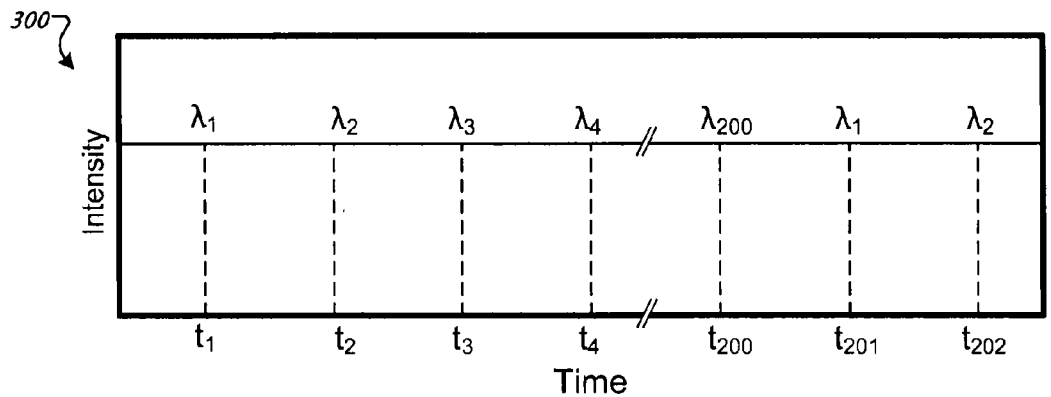
FIGS. 3A-C show examples of the wavelength sweep cycle transmitted by a sweep

A sweep sensor may include a signal source, a propagation medium, and a detector. By transmitting an interrogating signal from the signal source into the propagation medium, detectable disturbances along the medium can physically alter the characteristics of the medium, which may cause a measurable change in the backscattered signal at the detector. Based on the change, it may be possible to locate the geographic origins of the physical disturbances along the propagation medium, or to determine the nature of the disturbances, or both. For example, it is generally possible to estimate the approximate distance between the detector and the disturbance given the time required to obtain the backscattered signal and the velocity of the signal source in the propagation medium. Further, in some embodiments, it is possible to quantify the amount of disturbance. In some implementations, the sweep sensor may be deployed as an intrusion detection sensor around the perimeter of a restricted area, for example an airport, a nuclear power plant, or a military base, to alert the security personnel of any unauthorized entry. Such implementations may place the propagation medium underground or along a fence. In other implementations, the sweep sensor may be disposed substantially close to fluid-transporting pipes, such as petroleum or natural gas pipes, to detect encroachment, excavation, leaks, and breaks. In another implementation, the sweep sensor may be deployed as a temperature sensor for applications such as distributed fire detection, pipeline leak detection, or downhole sensing.

In many traditional fiber optic sensors for detection, the sensitivity and/or length of the sensor may be limited by its signal-to-noise ratio (SNR). A sensor using a single mode light source may detect randomly-generated noises in the backscattered signal originating from the optical source fluctuations and/or inherent defects in optical fiber. Such noises can mask the intended signal and decrease the SNR, effectively limiting the sensitivity and range of the sensors. In some implementations, the sweep sensor includes a wavelength-tunable light source that transmits interrogating signals of different wavelengths into the detection area. As such, the SNR of the sweep sensor may be greater than 100:1, and in particular embodiments, greater than 1000:1.

Referring to an example sweep sensor 100 shown in FIG. 1, a coherent light source 110 transmits a wavelength-tunable interrogating signal into a first optical fiber 120a. The two ends of the first optical fiber 120a are coupled separately to the coherent light source 110 and a first terminal 132a of a coupler 130. The interrogating signal entering the first terminal 132a can exit the coupler 130 via a second terminal 132b and inject into a second optical fiber 120b. A portion of the second optical fiber 120b can be disposed in a detection area 160. In some circumstances, the interrogating signal may propagate along the second optical fiber 120b until contacting a first optical fiber terminator 140, which substantially reduces back reflections at the end of the second optical fiber 120b. In some implementations, physical disturbances and/or defects in the second optical fiber 120b can cause some of the interrogating signal in the second optical fiber 120b to backscatter in the opposite direction of the interrogating signals. Accordingly, the backscattered signal propagates along the second optical fiber 120b back into the second terminal 132b of the coupler 130. Similar to the first interrogating signal, the backscattered signal can exit a third terminal 132c and into a third optical fiber 120c, and propagates until reaching a detector 170. By evaluating the correlation among the backscattered signals, it is possible to determine the presence, and the location of physical disturbances in the detection area 160.

Referring now to another example sweep sensor 200 shown in FIG. 2, in some implementations, a light source 210 includes a light emitter 212, a modulator 214, and an amplifier 216. The light emitter 212 can output a continuous, wavelength-tunable coherent light wave into the modulator 214. Examples of devices capable of performing the function of the light emitter 212 include a semiconductor diode laser (e.g. III-V laser diode, vertical cavity surface emitting laser, or quantum well laser), a external cavity diode laser, a fiber laser, a solid state laser (e.g. Neodymium:Yttrium Aluminum Garnet laser), a gas laser (e.g. Helium Neon and Argon) or other appropriate lasers with suitable narrow spectral linewidths. The light emitter 212 can output a continuous light wave into the modulator 214, which may modulate the continuous light wave into one or more similar or dissimilar pulses by periodically changing the intensity of the continuous light wave. In some implementations, the modulator 214 may be an electro-optic device (e.g. Lithium Niobate device). Other possible devices for the modulator 214 may include an acousto-optic device (e.g. Bragg cell) or a semiconducting optical amplifier used as an optical switch, for example. Next the pulses propagate through the amplifier 216, which can increase the signal intensity of the pulses. Examples of the amplifier 216 can include a doped optical fiber amplifier or a semiconductor amplifier. Other types of devices are possible. Subsequently, the light source 210 transmits the amplified pulses into a first optical fiber 220a. As the interrogating pulses propagate through the first optical fiber 220a and into a first terminal 232a, a coupler 230 can transmit each individual interrogating pulse to exit the coupler 230 via a second terminal 232b to enter into a second optical fiber 220b. In some implementations, the coupler may be an optical circulator. In other implementations, the coupler may be a 3-dB coupler. The interrogating signal inputting into the second optical fiber 220b can include one or more light pulses. A first optical fiber terminator 240 can minimize the reflected light pulses from the end of the second optical fiber, thus reducing the intensity of light pulses reflected from outside a detection area 260. The first optical fiber terminator 240 may reduce the noise signals inside the sweep sensor 200, for example. In some embodiments, the first optical fiber terminator 240 may include bending some portions of the end of the second optical fibers 220b past its critical bend radius. As such, the interrogating signals reaching the first optical fiber terminator 240 can leak out of the second optical fiber 220b instead of reflecting back into the sweep sensor 200. In alternative embodiments, the optical fiber terminator 240 may be an optical isolator based on a Faraday rotator with polarizing elements. In some embodiments, the second optical fiber 220b can be unterminated.

Still referring to FIG. 2, some embodiments of the sweep sensor 200 may dispose the second optical fiber 220b in the detection area 260. A length 262 of the detection area 260 may range from about 1 m to about 100 km, from about 100 m to about 10 km, or from about 5 km to about 30 km. Other ranges are possible. The pulse width and the transmission frequency of the interrogating pulses may depend on the length of the second optical fiber 220b or on the length of the detection area 260. In some implementations, interrogating pulses propagating in the second optical fiber 220b within the detection area 260 may backscatter from locations affected by detectable physical disturbances, which may include temperature fluctuation or vibration near the second optical fiber 220b and distortion or displacement of the second optical fiber 220b. Backscattered light pulses can propagate along the second optical fiber 220b, in the opposite direction of the interrogating pulses, back to the coupler 230. Next, the backscattered light pulses can enter a third optical fiber 220c through a third terminal 232c, and subsequently into a detector 270. In selective embodiments, the optical fibers 220 may be single mode optical fibers. Examples of devices for the detector 270 include one or more photodiodes, avalanche photodiodes, phototransistors, charge-coupled devices, pyroelectric detectors, and photomultipliers. Other photo-detectors capable of sensing the backscattered light pulses may be used.

In some implementations, the detector 270 may include a suitable photodetector, an optical pre-amplifier, an electronic amplifier, a signal digitizer, and a processor. The processor may include a computer-readable medium with a storage medium for storing data and a processing unit for analyzing the backscattered light pulses. In some implementations, the detector 270 may include a plurality of detectors, arranged to implement diversity detection or differential or biased detection, for example.

In some implementations, during the operation of the sweep sensor, the light emitter 212 may modulate one or more parameters of the interrogating light wave. For example, as shown in a first graph 300 of FIG. 3A, the wavelengths of the interrogating light wave may vary deterministically with time, from $\lambda_1$ at $t_1$, to $\lambda_2$ at $t_2$, to $\lambda_3$ at $t_3$, to $\lambda_4$ at $t_4$, and sequentially to $\lambda_{200}$ at $t_{200}$, and back to $\lambda_1$ at $t_{201}$ to repeat a wavelength sweep cycle. The wavelengths $\lambda_1, \lambda_2, \lambda_3, \lambda_4 \ldots$ and $\lambda_{200}$ may be evenly divided into a wavelength sweep range, i.e. $\lambda_2 = \lambda_1 + \Delta\lambda, \lambda_3 = \lambda_1 + 2\Delta\lambda, \lambda_4 = \lambda_1 + 3\Delta\lambda, \ldots \lambda_{200} = \lambda_1 + 199\Delta\lambda$. In some implementations, $\Delta\lambda$ may range from about 1 femtometer to about 100 femtometers, or about 5 femtometers to about 50 femtometers, for example, or about 10 femtometers. Accordingly, the wavelength sweep range may be from approximately 100 femtometers to approximately 10 picometers, or approximately 600 femtometers to approximately 5 picometers, and in a selective embodiment, about 1 picometer. For example, the wavelengths of the light pulse from the light source 210 may transmit light waves centered at about 1500 nm. The wavelength range of the light can depend on the light emitter 212 or the modulator 214 or both, and can include any suitable range which may provide a sampling of constructive and destructive interference conditions for locally backscattered light waves.

Figure 3B:
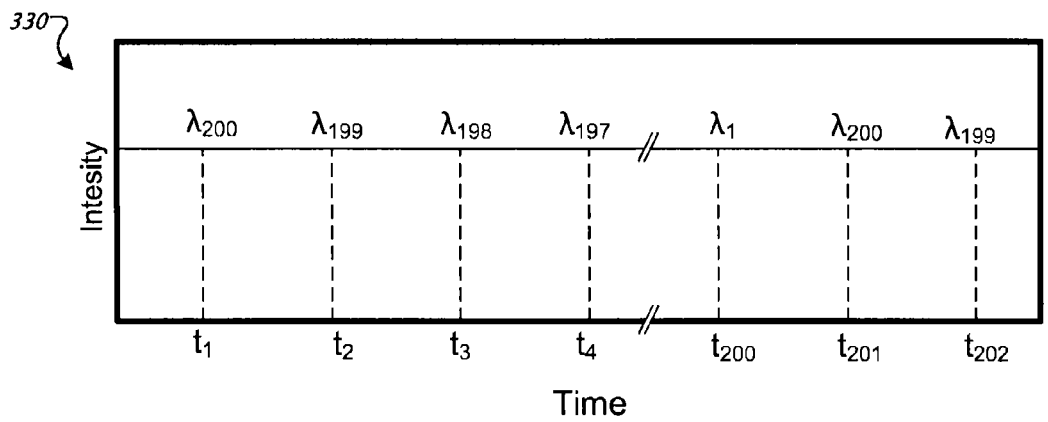

As shown in the first graph 300 in FIG. 3A, such wavelength sweep cycles may begin with the shortest wavelength light, $\lambda_1$, and end with the longest wavelength light $\lambda_{200}$, for example. Alternatively, as illustrated in a second graph 330 in FIG. 3B, the wavelength sweep cycle may begin with the longest wavelength light, $\lambda_{200}$, and end with the shortest wavelength light $\lambda_1$, i.e. the wavelength of the light vary from $\lambda_{200}$ at $t_1$, to $\lambda_{199}$ at $t_2$, to $\lambda_{198}$ at $t_3$, to $\lambda_{197}$ at $t_4$, and sequentially to $\lambda_1$ at $t_{200}$, and back to $\lambda_{200}$ at $t_{201}$. In another example, the wavelength sweep cycle may alternate ascending and descending sweepings of wavelengths (e.g. $\lambda_1$ at $t_1 \ldots \lambda_{200}$ at $t_{200}, \lambda_{199}$ at $t_{201}$, and back to $\lambda_1$ at $t_{400}$). In a further example, the number of wavelengths in the wavelength sweep cycle may range from about 100 (e.g. $\lambda_1, \lambda_2, \lambda_3, \ldots \lambda_{100}$) to about 160 (e.g. $\lambda_1, \lambda_2, \lambda_3, \ldots \lambda_{160}$), from about 150 ($\lambda_1, \lambda_2, \lambda_3, \ldots \lambda_{150}$) to about 240 ($\lambda_1, \lambda_2, \lambda_3, \ldots \lambda_{240}$). Other variants are possible. In yet another implementation, the wavelengths in a wavelength range may be divided unevenly.

Figure 3C:
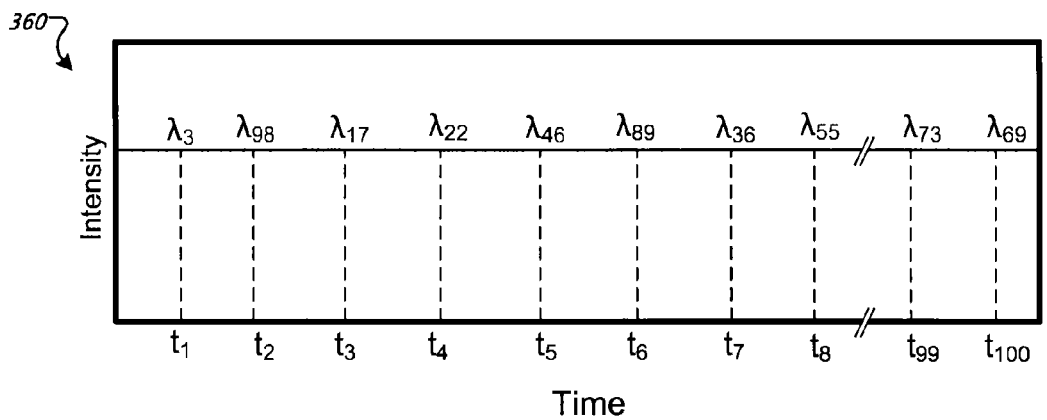

In some implementations, the wavelengths of the emitted interrogating light wave may be randomized by causing the instantaneous wavelength to change in a nondeterministic or an asynchronous manner. An example of such wavelength randomization is shown in a third graph 360 in FIG. 3C.

Now referring to FIGS. 2 and 4A, in some embodiments of the sweep sensor 200, the light source 210 may launch one or more pulses with dissimilar wavelengths. An example of a portion of the interrogating signal, as illustrated in a first graph 400 in FIG. 4A, may include a number of emitted pulses 405, or a packet 410, where each emitted pulse 405 in the packet 410 can carry a generally different wavelength (e.g. a first emitted pulse 405aa has a wavelength of $\lambda_1$, a second emitted pulse 405ab has a wavelength of $\lambda_2$, a third emitted pulse 405ac has a wavelength of $\lambda_3$, a fourth emitted pulse 405ad has a wavelength of $\lambda_4$ ... and a two hundredth emitted pulse 405gr has a wavelength of $\lambda_{200}$). In another example, the packet may include four hundred emitted pulses, where every two emitted pulses have substantially similar wavelengths. In yet another example, one or more emitted pulses in a packet may each carry more than one wavelength. Other combinations of emitted pulses and wavelengths are possible. During the operation of the sweep sensor 200, the light source 210 may send one or more packets 410 into the first optical fiber 220a. Emitted pulses may backscatter in the second optical fiber 220b in the detection area 260, and traverse back to the detector 270 according to the path described previously, where the detector 270 collects the backscattered pulses, or traces. The pulse widths and duty cycles are exaggerated for illustrative purposes and may vary according to the implementations discussed.

Still referring to FIG. 4A, in some implementations, the emitted pulses 405 transmitted by the light source 210 may include a 100 nanoseconds pulse. In other implementations, the pulse width may range from about 10 nanoseconds to about 1000 nanoseconds, and in particular embodiments, may range from about 50 nanoseconds to about 200 nanoseconds. Other pulse widths are possible. In selective embodiments, the shapes of the emitted pulses 405 in the packet 410 may be generally similar, and include a rectangular profile. In alternative embodiments, each emitted pulse 405 in the packet 410 may include substantially similar or dissimilar shapes, pulse widths, or separations from neighboring emitted pulses 405. Further, the packet 410 may include about 100 pulses to about 160 pulses, about 150 pulses to about 240 pulses, and in a particular embodiment, 200 pulses.

In some embodiments of the sweep sensor 200, the separation time between the emitted pulses 405 may be related with the length of the sweep sensor 200. After the first emitted pulse 405aa is transmitted into the first optical fiber 220a, the second emitted pulse 405ab may be transmitted after all backscattered light from the first emitted pulse 405aa has reached the detector 270 or has exited the detection area. Accordingly, the separation time can be substantially similar to the round-trip time (i.e. time for the emitted light in pulses 405 to traverse the sweep sensor 200, and return as backscatter to the detector 270). Alternatively, the separation time between the emitted pulses 405 may be longer or shorter than the round-trip time of light in the sweep sensor 200.

Now referring to FIGS. 2 and 4A-E, FIGS. 4B-E show in illustrative diagrams examples of detected traces 425, 445, 465, 485 constructed from the backscattering of the emitted pulses 405 in the sweep sensor 200 for a location along the second optical fiber 220b within the detection area 260. The ordinates of a second, third, fourth, and fifth graphs 420, 440, 460, 480 represent the intensities of the traces 425, 445, 465, and 485, respectively, while the abscissas represent the wavelengths of the emitted pulses. Specifically, using the second graph 420 of FIG. 4B as an illustrative example, each trace 425 may represent the backscattered intensities of emitted pulses 405 within the packet 410, plotted against the wavelengths of the emitted pulses 405, for a location along the second optical fiber 220b. For example, to obtain the first trace 425aa, the light source 210 can send one packet of interrogating pulses, which can cover a wavelength sweep cycle, into the sweep sensor 200. The intensity of the backscattered signal collected at the detector 270 after a fixed time interval following the emission of each pulse 405 can be used to construct the first trace 425aa against the swept wavelength for a location along the second optical fiber 220b with light round-trip time corresponding to said fixed time interval. The spatial extent of the location so interrogated is related to the width of the emitted pulses and the bandwidth of the detector 270. Each trace 425 may represent a packet of backscattered pulses transmitted with deterministically different wavelengths (e.g. one hundred packets sent into the sensor can generate one hundred traces). In general, if the light source 210 transmits two hundred emitted pulses 405, each with a different wavelength, then the detector may correspondingly receive two hundred backscattered pulses, which can construct one trace, for example. The second graph 420 in FIG. 4B illustrates an example of traces 425 when the second optical fiber 220b experiences minimum detectable physical disturbance at the said location. The traces 425 substantially have similar shapes, and overlap in the relative time domain. As such, the traces 425 in FIG. 4B are highly correlated, which can indicate minimum detectable physical disturbance at the said location in the detection area 260.

Referring to the third graph 440 in FIG. 4C, the traces 445 have substantially similar shapes, and include lateral shifts along the wavelength domain (e.g. as is evident in comparison of the first trace 445aa to the third trace 445ac). Such traces can be intermediately correlated, and indicate slow drifting or uniform physical disturbances, for example, such as ambient temperature change, strain fluctuation, slow displacement or change in load condition near a location in the second optical fiber 220b, represented by the traces 445 of the third graph 440. Based on the shifts among the traces 445, it may be possible to quantitatively determine the amount of temperature change, for example.

Referring more closely to the fourth graph 460 in FIG. 4D, the first, second, ninety-ninth and one hundredth traces 465aa, 465ab, 465du, 465dv have generally similar shapes, corresponding to substantially similar initial and final steady-state conditions. The remaining traces 465 are minimally correlated and may represent the backscattered signal during the presence of fast physical disturbances. Specifically, the first and second traces 465aa, 465ab may indicate minimum detectable physical disturbances at a location in the detection area 260. The third, and fourth traces 465ac, 465ad show random fluctuations in the intensities of the backscattered signals, which may indicate the presence of physical disturbances occurring on the time scale comparable to or faster than the time intervals between the traces 465. The ninety-ninth and one hundredth traces 465du, 465dv substantially restores to the generally similar shape as the first and second traces 465aa, 465ab, which indicates the removal of fast physical disturbances. Such evolution may indicate the presence of reversible fast physical disturbances, such as fast vibration, in a location in the detection area 260. The magnitude of said physical disturbances may be estimated by the degree of correlation between trace 460, ranging from substantially full correlation of 1 to minimal correlation of 0.

Referring now to the fifth graph 480 in FIG. 4E, the first and second traces 485aa, 485ab have a generally similar first shape, and the ninety-ninth and one hundredth traces 485du, 485dv have a generally similar second shape. The remaining traces 485 are minimally correlated and may represent the backscattered signal during the presence of fast physical disturbances. Such evolution may indicate the presence of irreversible physical disturbances, such as displacement or change in load conditions, at 10 a location in the detection area 260.

As stated above, examples of fast physical disturbances include fast vibration (e.g. a potential intruder walking near the second optical fiber 220b) and displacement (e.g. a potential intruder stepping directly on or digging underneath a buried optical fiber, or physically touching an above-ground fiber-optic cable). Other contributing factors may also cause the detected traces 465 to be minimally correlated. In FIGS. 4A-E, the shapes, durations, and wavelength shifts of the pulses 405 and the traces 425, 445, 465, 485 are for purposes of illustration and may vary. A number of known methods may be used to compute correlation such as Pearson Correlation and Brownian Correlation, for example. Other approaches to quantifying the differences between the detected traces may also be used.

Figure 5A:
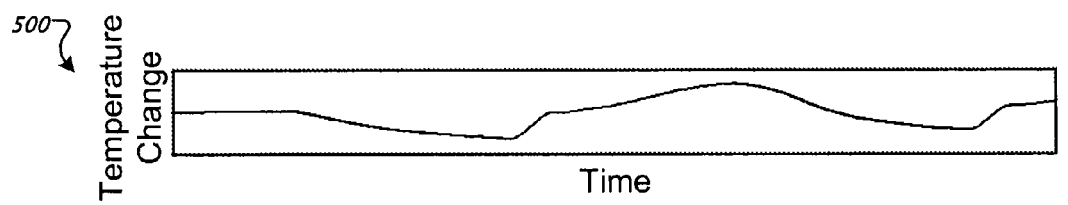
FIGS. 5A-E show examples of temperature measurement and correlation measurement based on the detected traces.

Referring to FIGS. 2 and 5A, the first temperature graph 500 shows an example measurement of temperature change at a location along the second optical fiber 220b in the detection area 260 by quantifying the shift in the detected traces, such as the traces 445 shown in FIG. 4C.

Figure 5B:
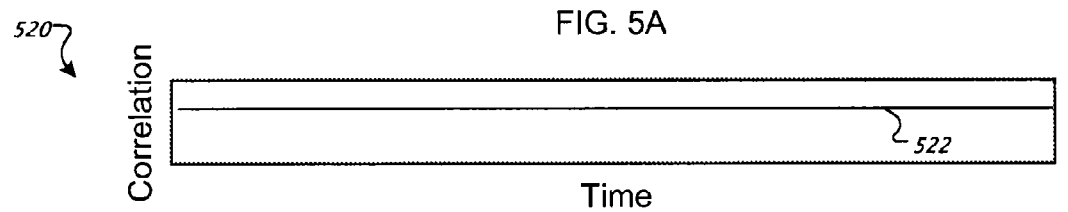
Figure 5C:
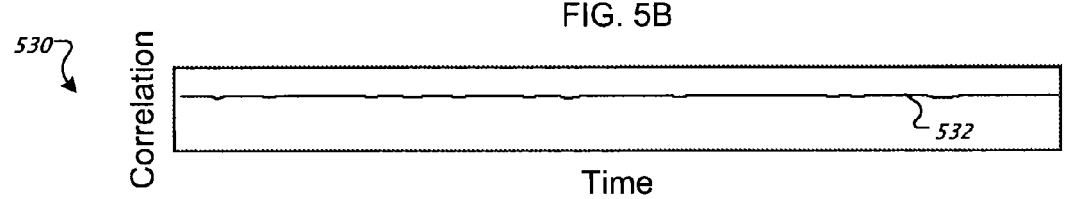
Figure 5D:
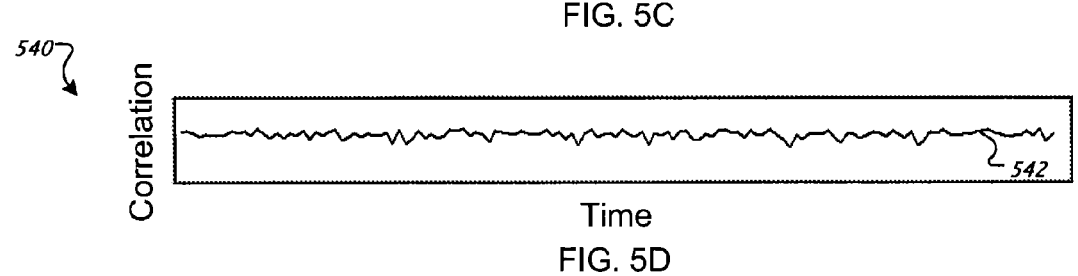
Figure 5E:
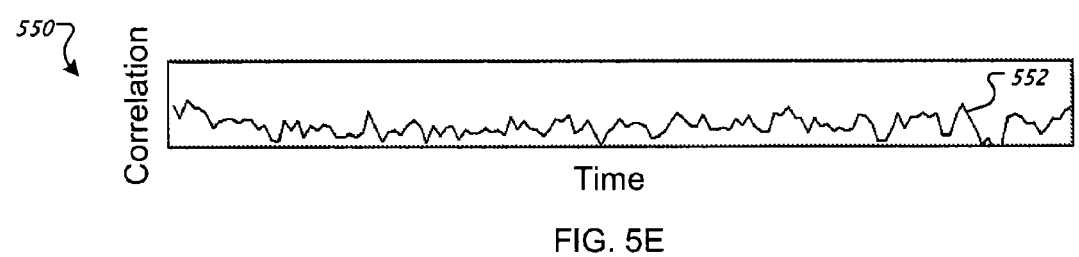

Referring now to FIGS. 5B-E, as an example illustration of the functionality of an implementation of a sweep sensor, such as the sweep sensor 200 described in relation to FIG. 2, a mechanical machinery used for digging trench is disposed near the second optical fiber 220b without making physical contact to the second optical fiber 220b. FIGS. 5B-E include a first, second, third, and fourth correlation graphs 520, 530, 540, 550 which illustrate, respectively, a first, second, third, and fourth correlation curves 522, 532, 542, 552. During the measurement of the second correlation curve 522, as illustrated in FIG. 5B, the mechanical machinery remains in the off state, in which the sweep sensor 200 detects no disturbance (i.e. highly correlated traces). The third, fourth, and fifth correlation curves 532, 542, 552, as illustrated in FIGS. 5C-E, show example detections during three states of operation of the mechanical machinery: activation of motor, engagement of chainsaw, and digging, respectively, showing progressively reduced correlation in accordance with the magnitude of disturbance.

Figure 6A:
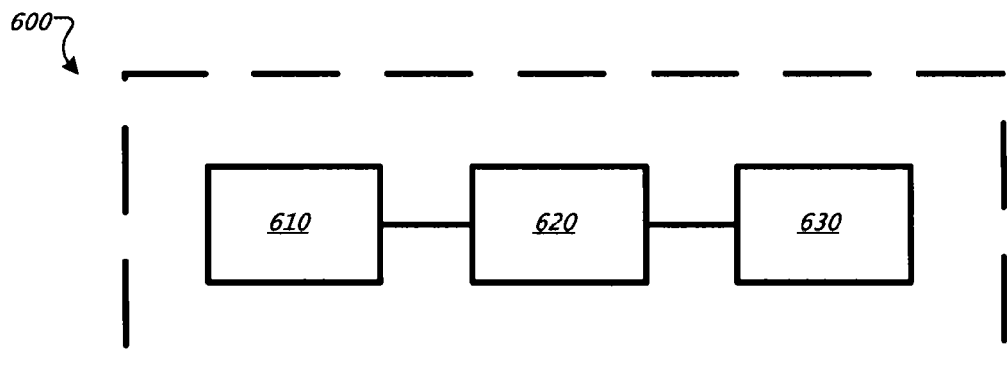
FIGS. 6A-C show three example implementations of a light source used in a sweep sensor.
Figure 6B:
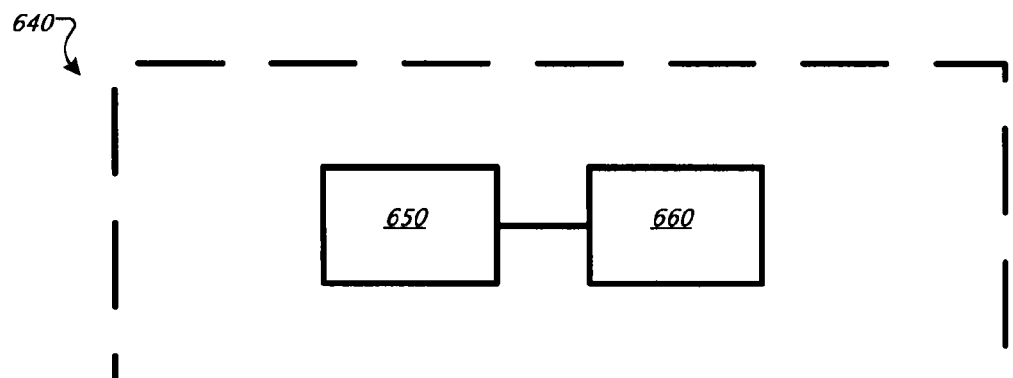
Figure 6C:
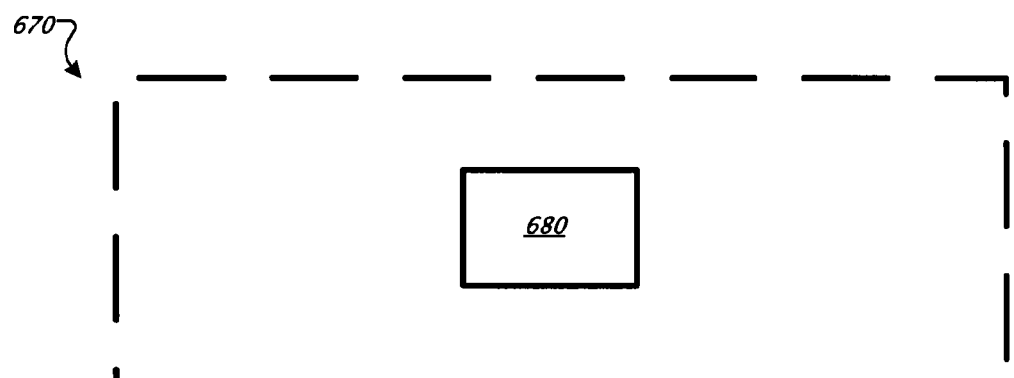

FIGS. 6A-C show exemplary embodiments of light sources 600, 640, 670 that may generate the interrogating pulses appropriate for the coherent light source 110 shown in FIG. 1 (or the light source 210 in FIG. 2). In some implementations, the light source 600 may include a light emitter 610, a modulator 620, and an amplifier 630. The wavelengths of the continuous coherent light wave can be controlled in the light emitter 610 by changing the drive current, device temperature, or cavity length of the light emitter 610, for example. Alternatively, the wavelengths of the light wave may be controlled at the modulator 620 by changing the electric field applied to an electro-optic modulator, or changing the vibration frequency applied to an acousto-optic modulator. In some implementations, the interrogating signal may include pulses modulated by changing the drive current of the light emitter 610, the shutter state of the modulator 620 (e.g. Q-switch), or the external stimuli (e.g. electric field or vibration) applied to the modulator 620 (e.g. electro-optic or acousto-optic) as described above. As the interrogating pulses exit the modulator 620, the amplifier 630 may increase the intensities of the pulses when pumped optically or electrically by an external source (not shown). Examples of the amplifier 630 include a doped optical fiber amplifier (e.g. erbium doped optical fiber amplifier) and a semiconductor optical amplifier.

In other implementations, the light source 640 may include a light emitter 650 and a modulator 660 as shown in FIG. 6B. For example, the light emitter 650 may include a solid state laser described above, and the modulator 660 can provide means for changing the wavelengths of the continuous light wave and generating the interrogating pulses. For example, the modulator 660 may include an acousto-optic device described above for the wavelength modulation, and an electro-optic device to generate the interrogating pulses.

In additional implementations, as shown in FIG. 6C, the light source 670 may include a light emitter 680 that directly emits interrogating pulses, such as pulses with varying wavelengths for example. Other combinations of the light emitter, modulator, and amplifier may generate appropriate interrogating pulses for a sweep sensor such as the sweep sensors 100 and 200.

Referring to FIG. 7, an example of a sweep sensor 700 may include a light source 710 and a polarization controller such as ones illustrated in U.S. Provisional Application No. 61/000,968 entitled "Fiber optic intrusion detection system based on coherent OTDR" filed on Oct. 30, 2007, hereby incorporated by reference in its entirety. In some implementations, the light source 710 emits an interrogating signal into a polarization controller 718 for polarization management. The interrogating signal may include pulses with substantially different wavelengths, as described above. Next, the interrogating signal propagates into a first optical fiber 720*a*. The two ends of the first optical fiber 720*a* are coupled separately to the polarization controller 718 and a first terminal 732*a* of a coupler 730. The interrogating signal entering the first terminal 732*a* can exit the coupler 730 via a second terminal 732*b* and injects into a second optical fiber 720*b*. A portion of the second optical fiber 720*b* can be disposed in a detection area 760. In some circumstances, physical disturbances or defects in the second optical fiber 720*b* or both in the detection area 760 can cause some of the interrogating signal in the second optical fiber 720*b* to backscatter in the opposite direction of the interrogating signals, while the remaining interrogating signal may propagate along the second optical fiber 720*b* until contacting a first optical fiber terminator 740. Accordingly, the backscattered signal propagates along the second optical fiber 720*b* back into the second terminal 732*b* of the coupler 730. The backscattered signal can exit a third terminal 732*c* and into a third optical fiber 720*c*, and propagates until reaching a detector 770. As shown in an example graph 800 in FIG. 8, adjusting the states of polarization (SOP) of the interrogating signal may reduce polarization-induced signal fading of the backscattered signal. For example, the polarization-induced signal fading occurs within approximately a first time frame 810 when the input coherent signal has a first SOP 820. If the input polarization state changes to a second SOP 830, the polarization induced signal fading within the first time frame 810 can be avoided. Methods of managing the SOP include polarization scrambling, polarization modulation, and polarization dithering, for example. In some implementations, the interrogating pulses may include light waves of generally different pulse profiles, such as wavelength, chirp, phase, pulse width, pulse shape, and SOP, as described in U.S. Provisional Application No. 61/283,019 entitled "Wavelength sweep fiber optic sensor" filed on Nov. 25, 2009 and 61/335,575 entitled "Wavelength sweep fiber optic sensor" filed on Jan. 8, 2010, each of which is hereby incorporated by reference in its entirety. For example, in a packet of interrogating pulses, each pulse may include light wave of a generally different SOP. Furthermore, each pulse may include more than one distinct pulse profile (e.g. wavelength and SOP). In some implementations, a pulse may include more than one wavelength or a variable wavelength chirp. Wavelength, chirp, phase, pulse width, pulse shape, and SOP may be modulated by the light emitter, modulator, polarization controller or any combination of the three devices. Other pulse profiles of the light wave may be altered for each interrogating pulse in a packet.

Figure 9:
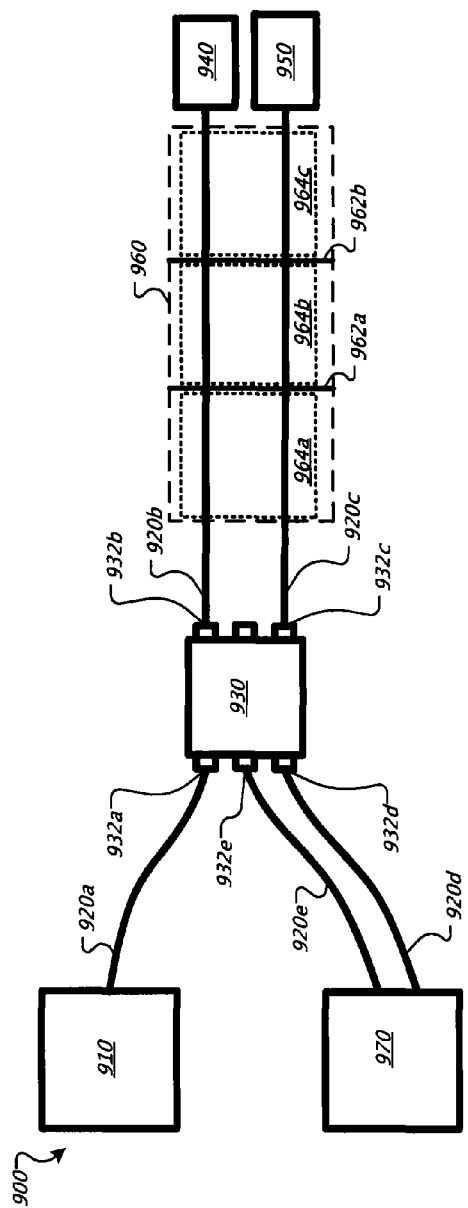
FIG. 9 illustrates yet another implementation of a sweep sensor.

FIG. 9 illustrates an example of a sweep sensor 900 such as ones described in U.S. Provisional Application Nos. 61/069,496 entitled "Distributed Michelson intrusion detection sensor" filed on March 14 and 61/207,274 entitled "Distributed fiber optic sensor" filed on February 10, each of which is hereby incorporated by reference in its entirety. In some implementations, the sweep sensor 900 may include a light source 910 which emits an interrogating signal formed substantially of pulses with generally different wavelengths, as described above. Next, the interrogating signal propagates into a first optical fiber 920*a*. The two ends of the first optical fiber 920*a* are coupled separately to the light source 910 and a first terminal 932*a* of a coupler 930. The interrogating signal entering the first terminal 932*a* of the coupler 930 can be split into three interrogating signals with similar or dissimilar amplitudes. After the split, two of the three interrogating signals can exit the coupler 930 via a second and a third terminal 932*b*, 932*c*, and inject into a second and a third optical fiber 920*b*, 920*c*, respectively. In selective embodiments, portions of at least one of the second and third optical fibers 920*b*, 920*c* can be disposed within the same or different cables in a detection area 960. In some circumstances, physical disturbances or defects in one or both of the optical fibers 920*b*, 920*c* in the detection area 960 can cause some of the interrogating signals in the second and/or third optical fibers 920*b*, 920*c* to backscatter in the opposite direction of the interrogating signals, while the remaining interrogating signals may propagate along the second and the third optical fibers 920*b*, 920*c* until contacting a first and a second optical fiber terminator 940, 950, respectively. Accordingly, the backscattered signals propagate along the second and/or third optical fibers 920*b*, 920*c* back into the second and/or third terminals 932*b*, 932*c* of the coupler 930, respectively. The backscattered signals can combine, interfere, and split into three backscattered signals with similar or dissimilar amplitudes and potentially with a different phase bias for each of the three split signals. One of the three split signals exits the first terminal 932*a* and injects into the first optical fiber 920*a*, while the other two split signals exit a fourth and a fifth terminal 932*d*, 932*e* and into a fourth and a fifth optical fiber 920*d*, 920*e*. Each of the other two split signals propagates until reaching a detector 970. Detector 970 may be configured to measure the relative phase between the two backscattered signals combined at the coupler 930, as described in the U.S. Pat. No. 7,725,026, filed on Apr. 1, 2005, entitled "Phase responsive optical fiber sensor", hereby incorporated by reference in its entirety.

In some embodiments, the sweep sensor 900 may be able to detect one or more simultaneous disturbances in the detection area. For example, as the split interrogating signals propagate along the second and third optical fibers 920*b*, 920*c*, physical disturbances occurring in a first and a second event site 962*a*, 962*b* can cause detectable differences in the phase information of the backscattered signals along the length of the second and third optical fibers 920*b*, 920*c*. Specifically, disturbances at the first and second event sites 962*a*, 962*b* have minimum effect on the phase information of the interrogating signals backscattered in a first sector 964*a*. Disturbances at the first event site 962*a* can change the phase information of the interrogating signals backscattered in a second and a third sector 964*b*, 964*c* as the interrogating signals propagate through the event sites 962. Similarly, disturbances at the second event site 962*b* can cumulatively change the phase information of the interrogating signals backscattered in the third sector 964*c*. In some implementations, the backscattered signals inject into the detector 970 via the fourth and fifth optical fibers 920*d*, 920*e*. By analyzing the phase information of the backscattered signals, it is possible to detect multiple disturbances in the detection area 960 with the sweep sensor 900. In other implementations, a polarization controller (not shown in FIG. 9) may be inserted between the light source 910 and the first optical fiber 920*a* to manage the SOP of the interrogating signals prior to entering the detection area 960.

Figure 10:
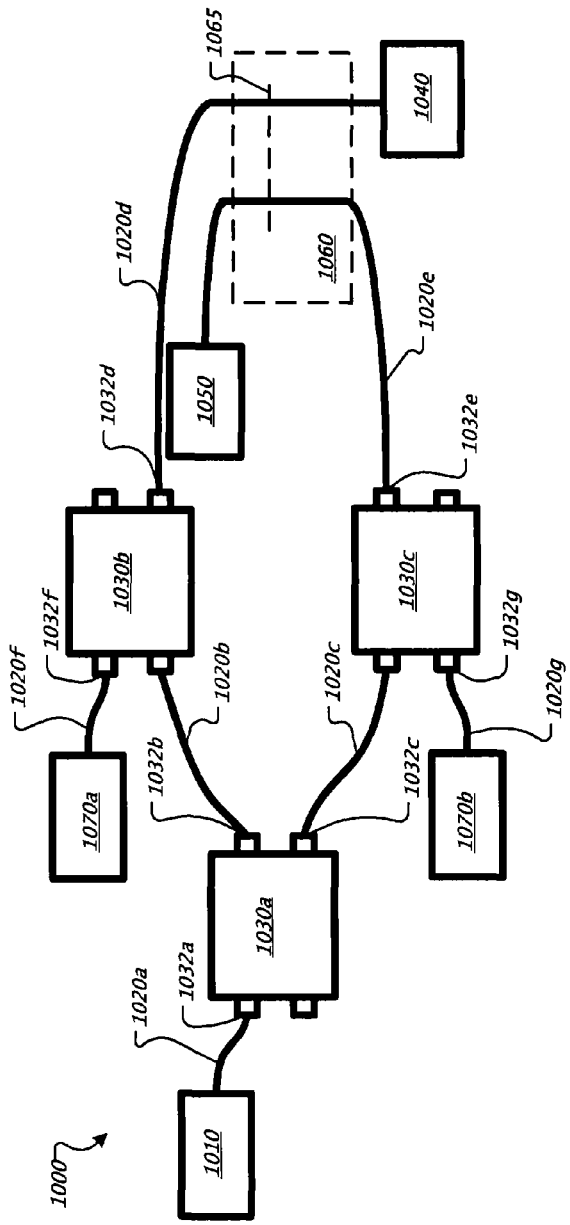
FIG. 10 illustrates another implementation of a sweep sensor.

In some embodiments, a sweep sensor may include two opposing detection optical fibers to detect phase information of the backscattered signal, such as ones described in U.S. Provisional Application Nos. 61/065,600 entitled "Distributed fiber optic perimeter intrusion detection system with failover capability" filed on Feb. 13, 2008 and 61/195,762 entitled "Distributed fiber intrusion detection sensor" filed on Oct. 10, 2008, each of which is hereby incorporated by reference in its entirety. Referring to FIG. 10, a sweep sensor 1000 may include a light source 1010 which emits an interrogating signal that includes pulses with substantially different wavelengths, as described above. Next, the interrogating signal propagates into a first optical fiber 1020a, then into a first terminal 1032a of a first coupler 1030a, and subsequently can be split into two interrogating signals with similar or dissimilar amplitudes. After the split, the two interrogating signals can exit the first coupler 1030a via a second and a third terminal 1032b, 1032c, and inject into a second and a third optical fiber 1020b, 1020c, respectively. The two interrogating signals exit a fourth and a fifth terminal 1032d, 1032e and inject into a fourth and a fifth optical fiber 1020d, 1020e, which may be encased in the same or different cables. A portion of the fourth and the fifth optical fibers 1020d, 1020e can be disposed in a detection area 1060. In some circumstances, physical disturbances or defects in one or both of the fourth and fifth optical fibers 1020d, 1020e in the detection area 1060 can cause some of the interrogating signals to backscatter in the opposite direction of the interrogating signals, while the remaining interrogating signals may propagate along the fourth and the fifth optical fibers 1020d, 1020e until contacting a first and a second optical fiber terminator 1040, 1050, respectively. Accordingly, the backscattered signals propagate along the fourth and fifth optical fibers 1020d, 1020e back into the fourth and fifth terminals 1032d, 1032e of the second and a third coupler 1030b, 1030c, respectively. Next, the backscattered signals exit a sixth and a seventh terminals 1032f, 1032g, inject into a sixth and a seventh optical fiber 1020f, 1020g, and propagate until reaching a first and a second detector 1070a, 1070b, respectively.

Figure 12:
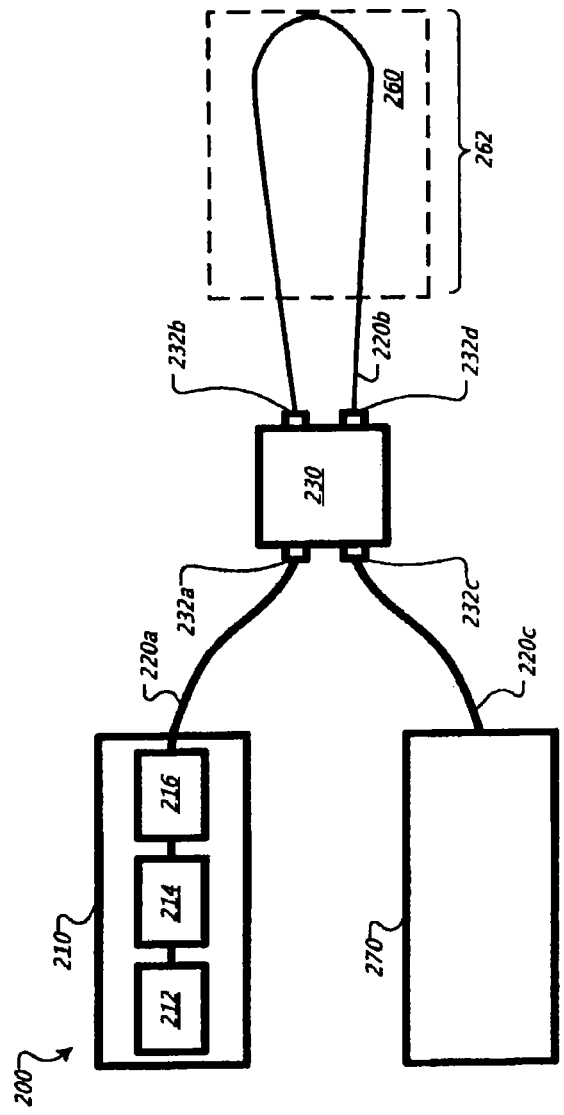
FIG. 12 illustrates a failover capability of a sweep sensor according to FIG. 2.
Like reference symbols in the various drawings indicate like elements.

The configuration of the sweep sensor 1000, for example, may allow the continuingly proper function of the sweep sensor 1000 after an accidental or intentional disabling of the sweep sensor 1000. For example, a potential intruder may sever the one or more cable(s) encasing the interrogating fourth and fifth optical fibers 1020d, 1020e of the sweep sensor 1000. In an illustrated example, severing the cable(s) can disable the sensing capabilities of a portion of the fourth optical fiber 1020d, from a sever point 1065 to the first optical fiber terminator 1040, and/or a portion of the fifth optical fiber 1020e, from the sever point 1065 to the second optical fiber terminator 1050. However, the failover configuration, where two sensing optical fibers (i.e. fourth and fifth optical fiber 1020d, 1020e) are disposed overlappingly in the detection area 1060 in the opposite direction, can allow the sweep sensor 1000 to continue to detect physical disturbances in the detection area 1060. Specifically, the fourth and fifth optical fiber 1020d, 1020e can separately sense physical disturbances up to the sever point 1065, and maintain the sensing ability of substantially the entire detection area 1060. In another embodiment of the failover configuration, a single sensing optical fiber may be used as a back-up sensor to a main sensor. For example, as shown in FIG. 12, to implement the failover capability to the sweep sensor 200 shown in FIG. 2, the two ends of the second optical fiber 220b may connect directly to the second terminal 232b and a fourth terminal 232d (e.g., in a loop). The single sensing optical fiber may be disposed in the same cable as the main sensor, which can be one of the sweep sensors described above. As the a potential intruder severs the fiber cable, thus disabling a portion of the main sensor, an optical switch (not shown) may reroute the interrogating pulses to the severed single sensing optical fiber of the back-up sensor, for example. As such, the noninterfering signals may be propagated across the severed single optical fiber in opposite directions, effectively functioning similarly to the sweep sensor 1000 described in FIG. 10. Other configurations are possible, and may be integrated with previously described sensors structures.

In some implementations, a single direction sweep sensor, such as the sweep sensors 200, 700, 900 described previously, can detect a break in the sensing optical fiber, e.g. the second optical fibers 220b, 720b, 920b. More specifically, if a potential intruder cuts the second optical fiber 220b in the sweep sensor 200, some of the interrogating signals may reflect at the sever point (not shown), instead of propagating to the first optical fiber terminator 240. The sever point, which may be terminated differently than design, can generate a larger reflected signal than the optical fiber terminator 240. The increase in reflected signal may lead to an alarm (not shown) to alert the operator of the sweep sensor 200 regarding the potential sabotaging effort of the sweep sensor 200. Additionally, a break in the sensing optical fiber (e.g. the second optical fibers 220b, 720b, 920b) may reduce the backscatter time of the interrogating signal, which may be used to detect the presence of an intruder attempting to disable the sweep sensors 200, 700, 900, for example.

Figure 11A:
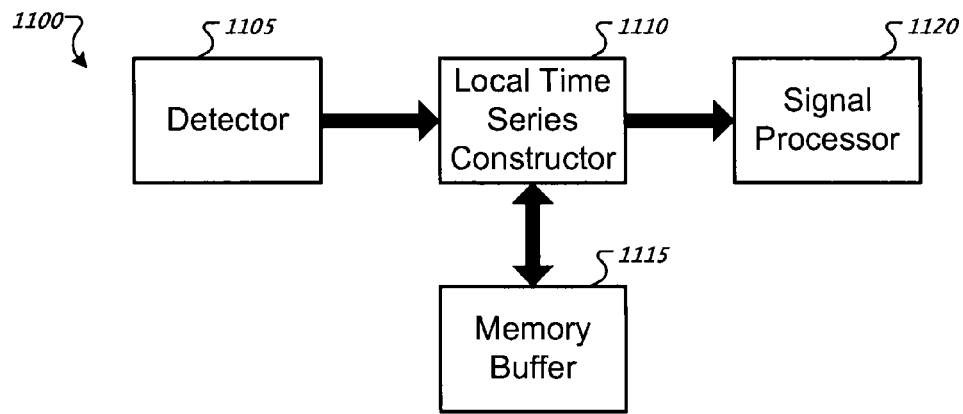
FIG. 11A is a block diagram illustrating a method of Local Time Series Reconstruction.
Figure 11B:
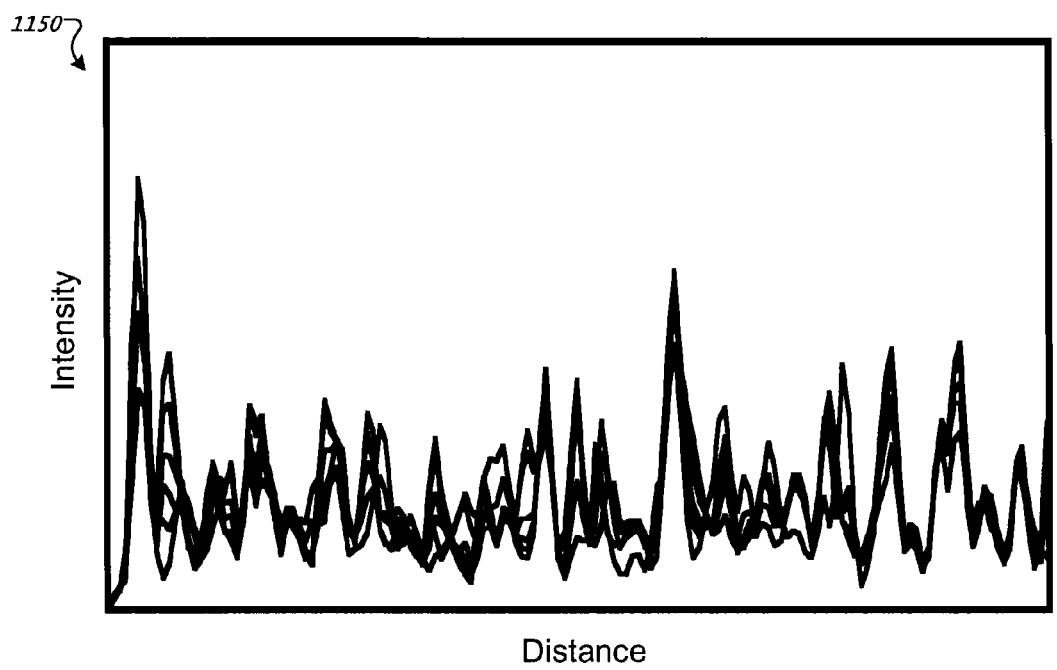
FIG. 11B shows an example diagram of collected pulses for the Local Time series Reconstruction.

FIG. 11A shows an implementation of the local time series (LTS) reconstruction system such as ones illustrated in U.S. Provisional Application No. 61/195,763 entitled "Local time series reconstruction for distributed fiber sensor" filed on Oct. 10, 2008, the entirety of which is herein incorporated by reference. A LTS reconstruction system 1100 can facilitate data processing of the traces detected by the detector 270 of the sweep sensor 200 shown in FIG. 2, for example. As shown in FIG. 11A, the LTS reconstruction system 1100 includes a detector 1105, such as the detector 270 in the sweep sensor 200, that transmits collected traces from the backscattering of the interrogating signals to a local time series constructor 1110. The local series constructor 1110 stores the collected traces on a memory buffer 1115 until a predefined amount of traces have been collected. Each trace, for example, represents the response of a packet of interrogating pulses backscattered from the detection area 260 during one wavelength sweep cycle. By superimposing two or more collected traces and normalizing to the detection area, a trace graph 1150 shown in FIG. 11B, may be constructed to plot the traces with respect to specific physical locations in the detection area (e.g., detection area 260). In some implementations, the trace graph 1150 plots an intensity of signal against a distance, from one edge of the detection area to another edge. The normalized traces may be sent to a signal processor 1120, such as one capable of performing signal processing techniques such as Fourier or Wavelet Transformations, to detect physical disturbances in the detection area. For example, applying the LTS reconstruction method to the sweep sensor 200 may improve the sensitivity of the sweep sensor 200 by minimizing or ignoring the contribution of noise.

A number of embodiments of the invention have been described. Nevertheless, it will be understood that various modifications may be made without departing from the spirit and scope of the invention. Accordingly, other embodiments are within the scope of the following claims.

What is claimed is:

1. A system for monitoring a detection area, comprising:
a coherent light source transmitting a first plurality of interrogating pulses, wherein
the first plurality of interrogating pulses includes a first subset of interrogating pulses and a second subset of interrogating pulses, the first subset of interrogating pulses comprising a substantially different pulse profile in relation to the second subset of interrogating pulses, the first subset of interrogating pulses being arranged in a deterministic fashion in relation to the second subset of interrogating pulses;
a first optical fiber of a first predetermined length disposed in the detection area;
a first coupler disposed between the coherent light source and the first optical fiber and coupled to the first optical fiber at a first terminal, wherein the first coupler is configured to:
provide the first plurality of interrogating pulses to the first optical fiber through the first terminal,
receive at least a first plurality of backscattered pulses generated in the first optical fiber as reflections of at least a portion the first plurality of interrogating pulses, and
provide the first plurality of backscattered pulses through a second terminal;
a second optical fiber of a second predetermined length coupled to the second terminal of the first coupler, the second optical fiber receiving the first plurality of backscattered light pulses from the first coupler; and
a first detector coupled to the second optical fiber, the first detector configured to:
receive the first plurality of backscattered pulses, and
analyze the first plurality of backscattered pulses to identify a first location of a first fast physical disturbance in the detection area, wherein
the first detector analyzes the first plurality of backscattered pulses based on intensity as a function of wavelength to determine a correlation among the first plurality of backscattered pulses.

2. A method for detecting a disturbance comprising:
transmitting a first plurality of interrogating pulses from a light source, the first plurality of interrogating pulses including a first subset of interrogating pulses and a second subset of interrogating pulses, the first subset of interrogating pulses comprising a substantially different pulse profile in relation to the second subset of interrogating pulses, the first subset of interrogating pulses being arranged in a deterministic fashion in relation to the second subset of interrogating pulses;
transmitting at least a second plurality of interrogating pulses from the light source, the second plurality of interrogating pulses including a third subset of interrogating pulses and a fourth subset of interrogating pulses, the third subset of interrogating pulses comprising a substantially different pulse profile in relation to the fourth subset of interrogating pulses, the third subset of interrogating pulses being arranged in a deterministic fashion in relation to the fourth subset of interrogating pulses;
transmitting the first plurality of interrogating pulses and the second plurality of interrogating pulses into a first optical fiber disposed in a detection area, wherein at least a portion of the first plurality of interrogating pulses generate a first plurality of backscattered pulses and at least a portion of the second plurality of interrogating pulses generate a second plurality of backscattered pulses;
receiving the first plurality of backscattered pulses and the second plurality of backscattered pulses at a detector;
collecting the first plurality of backscattered pulses and the second plurality of backscattered pulses in a storage medium; and
analyzing the first plurality of backscattered pulses and the second plurality of backscattered pulses, the analyzing comprising the steps of:
identifying a pulse profile associated with each of the first plurality of backscattered pulses and the second plurality of backscattered pulses, and
identifying intensity values in each of the first plurality of backscattered pulses and the second plurality of backscattered pulses corresponding to a first plurality of locations in the detection area,
for each of the first plurality of locations, performing the steps of:
constructing a first trace of the intensity values from the first plurality of backscattered pulses, where each intensity is associated with the pulse profile of a corresponding interrogating pulse of the first plurality of interrogating pulses,
constructing a second trace of the intensity values from the second plurality of backscattered pulses, where each intensity is associated with the pulse profile of a corresponding interrogating pulse of the second plurality of interrogating pulses,
comparing the first trace to at least the second trace,
quantifying a correlation between the first trace and the second trace, wherein the quantifying the correlation includes analyzing the first trace and the second trace based on intensity as a function of wavelength to determine the correlation between the first trace and the second trace, and
identifying a first location of a first fast physical disturbance in the detection area causing a difference between the first trace and the second trace.

3. An apparatus for detecting a physical disturbance comprising:
a coherent light source transmitting a light wave with periodically changing parameters, the light source generating a first sweep cycle including a first plurality of interrogating pulses and at least a second sweep cycle including a second plurality of interrogating pulses;
a first optical fiber of a predetermined length disposed in a detection area, wherein the first optical fiber receives the first sweep cycle and the second sweep cycle and reflects at least a portion of the first sweep cycle as a first backscattered sweep cycle including a first plurality of backscattered pulses and at least a portion of the second sweep cycle as a second backscattered sweep cycle including a second plurality of backscattered pulses; and
a detector configured to:
receive the first backscattered sweep cycle and the second backscattered sweep cycle from the first optical fiber;
beginning with the first backscattered sweep cycle and the second backscattered sweep cycle, perform iterative steps of:
identifying a pulse profile associated with each of the first plurality of backscattered pulses and the second plurality of backscattered pulses, identifying intensity values in each of the first plurality of backscattered pulses and the second plurality of backscattered pulses corresponding to a first plurality of locations in the detection area, constructing a first trace of the intensity values from the first plurality of backscattered pulses, where each intensity is associated with the pulse profile of a corresponding interrogating pulse of the first plurality of interrogating pulses, constructing a second trace of the intensity values from the second plurality of backscattered pulses, where each intensity is associated with the pulse profile of a corresponding interrogating pulse of the second plurality of interrogating pulses, comparing the first trace of the first backscattered sweep cycle to at least the second trace of the second backscattered sweep cycle, quantifying a correlation between the first backscattered sweep cycle and the second backscattered sweep cycle, wherein the quantifying the correlation includes analyzing the first backscattered sweep cycle and the second backscattered sweep cycle based on intensity as a function of wavelength to determine the correlation between the first backscattered sweep cycle and the second backscattered sweep cycle, and identifying a first location of a first fast physical disturbance in the detection area causing a difference between the first trace and the second trace.

4. The system of claim 1, wherein the first detector identifies the first location of the first fast physical disturbance by superimposing the first plurality of backscattered light pulses, normalizing to the detection area, and performing signal processing to the first plurality of backscattered light pulses.

5. The system of claim 1, further comprising a polarization controller disposed between the coherent light source and the first coupler, the polarization controller being configured to:
receive the first plurality of interrogating pulses,
manage states of polarization of the first plurality of interrogating pulses, and
transmit the first plurality of interrogating pulses to the first coupler, wherein the first plurality of interrogating pulses further includes a third subset of interrogating pulses and a fourth subset of interrogating pulses, the third subset of interrogating pulses comprising a substantially different state of polarization in relation to the fourth subset of interrogating pulses, the third subset of interrogating pulses being arranged in a deterministic fashion in relation to the fourth subset of interrogating pulses.

6. The system of claim 1, wherein the first detector is further configured to analyze the first plurality of backscattered pulses to identify a second location of a first slow physical disturbance in the detection area.

7. The system of claim 1, wherein
a first end of the first optical fiber is coupled to the first terminal of the first coupler,
a second end of the first optical fiber is coupled to a third terminal of the first coupler, and
the first coupler further provides the first plurality of interrogating pulses as at least a second plurality of interrogating pulses and a third plurality of interrogating pulses, the first coupler providing the second plurality of interrogating pulses to the first end of the first optical fiber and the third plurality of interrogating pulses to the second end of the first optical fiber.

8. The system of claim 1, further comprising a third optical fiber of a third predetermined length disposed in the detection area, the third optical fiber being coupled to a third terminal of the first coupler, wherein
the first coupler further provides the first plurality of interrogating pulses as at least a second plurality of interrogating pulses and a third plurality of interrogating pulses, providing the second plurality of interrogating pulses to the first optical fiber and the third plurality of interrogating pulses to the third optical fiber,
the first coupler receives a second plurality of backscattered pulses generated in the first optical fiber as reflections of at least a portion of the second plurality of interrogating pulses and a third plurality of backscattered pulses generated in the third optical fiber as reflections of at least a portion of the third plurality of interrogating pulses,
the first coupler provides the second plurality of backscattered pulses as at least a fourth plurality of backscattered pulses and the third plurality of backscattered pulses as at least a fifth plurality of backscattered pulses through the second terminal and a fourth terminal of the first coupler, and
the first detector receives the fourth plurality of backscattered pulses and the fifth plurality of backscattered pulses.

9. The system of claim 8, wherein the detector is further configured to analyze the fourth plurality of backscattered pulses and the fifth plurality of backscattered pulses to identify a second location of a second fast physical disturbance in the detection area.

10. The system of claim 1, further comprising a third optical fiber coupled to a third terminal of the first coupler, wherein
the first coupler further provides the first plurality of interrogating pulses as at least a second plurality of interrogating pulses and a third plurality of interrogating pulses, providing the second plurality of interrogating pulses to the first optical fiber and the third plurality of interrogating pulses to the third optical fiber,
a second coupler receives a second plurality of interrogating pulses from the first optical fiber, providing the second plurality of interrogating pulses to a fourth optical fiber to receive a second plurality of backscattered pulses generated in the fourth optical fiber as reflections of at least a portion of the second plurality of interrogating pulses,
a third coupler receives a third plurality of interrogating pulses from the third optical fiber, providing the third plurality of interrogating pulses to a fifth optical fiber to receive a third plurality of backscattered pulses generated in the fifth optical fiber as reflections of at least a portion of the third plurality of interrogating pulses,
the second coupler provides the second plurality of backscattered pulses to a sixth optical fiber,
the third coupler provides the third plurality of backscattered pulses to a seventh optical fiber,
a second detector coupled to the sixth optical fiber to receive the second plurality of backscattered pulses, and
a third detector coupled to the seventh optical fiber to receive the third plurality of backscattered pulses wherein the second plurality of interrogating pulses and the third plurality of interrogating pulses substantially propagate in opposing directions in the detection area.

11. The system of claim 1, wherein the coherent light source establishes the pulse profile by adjusting one or more of a wavelength, a phase, a pulse width, a pulse shape, and a state of polarization of the first subset of interrogating pulses in relation to the second subset of interrogating pulses.

12. The method of claim 2, wherein the analyzing further comprises the steps of quantifying a shift between the first trace and the second trace and identifying a second location of a first slow physical disturbance in the detection area causing a shift between the first trace and the second trace.

13. The method in claim 2, wherein the analyzing further comprises the step of identifying a third location of a physical disturbance causing a change from a first steady-state condition to a second steady-state condition.

14. The method in claim 2, wherein the analyzing further comprises the step of identifying a second plurality of locations of a plurality of disturbances in the detection area.

15. The method of claim 2, wherein the pulse profile is established by adjusting one or more of a wavelength, a phase, a pulse width, a pulse shape, and a state of polarization of the first subset of interrogating pulses in relation to the second subset of interrogating pulses.

16. The method of claim 2, further comprising managing states of polarization of the first plurality of interrogating pulses and the second plurality of interrogating pulses prior to transmitting the first plurality of interrogating pulses and the second plurality of interrogating pulses into the first optical fiber, wherein the managing includes applying a first state of polarization to a fifth subset of interrogating pulses and a second state of polarization substantially different than the first state of polarization to a sixth subset of interrogating pulses, and applying a third state of polarization to a seventh subset of interrogating pulses and a fourth state of polarization to an eighth subset of interrogating pulses.

17. The method of claim 16, wherein the first state of polarization, the second state of polarization, the third state of polarization, and the fourth state of polarization are established through one or more of polarization scrambling, polarization modulation, and polarization dithering.

18. The method of claim 2, wherein the analyzing further comprises the step of triggering an alarm in response to the identifying.

19. The apparatus of claim 3, wherein the first sweep cycle includes N number of interrogating pulses, wavelengths of the first plurality of interrogating pulses are one of increasing and decreasing in length between a first interrogating pulse and an Nth interrogating pulse.

20. The apparatus of claim 3, wherein a first pulse width of the first plurality of interrogating pulses and a second pulse width of the second plurality of interrogating pulses range from 50 nanoseconds to 200 nanoseconds.

* * * * *